(12) United States Patent
Novicki

(10) Patent No.: US 8,628,786 B2
(45) Date of Patent: *Jan. 14, 2014

(54) POLYCHLORINATED BIPHENYLS AND SQUALENE-CONTAINING ADJUVANTS

(75) Inventor: Deborah L. Novicki, Cambridge, MA (US)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/309,842

(22) Filed: Dec. 2, 2011

(65) Prior Publication Data

US 2012/0195931 A1    Aug. 2, 2012

Related U.S. Application Data

(63) Continuation of application No. 12/287,891, filed on Oct. 14, 2008, now Pat. No. 8,092,813.

(60) Provisional application No. 61/009,425, filed on Dec. 28, 2007.

(51) Int. Cl.
*A61K 39/00* (2006.01)

(52) U.S. Cl.
USPC ............................. 424/278.1; 424/283.1

(58) Field of Classification Search
None
See application file for complete search history.

(56) References Cited

U.S. PATENT DOCUMENTS

| | | |
|---|---|---|
| 4,011,313 A | 3/1977 | Thompson |
| 4,281,061 A | 7/1981 | Zuk et al. |
| 6,299,884 B1 | 10/2001 | Van Nest et al. |
| 6,623,739 B1 | 9/2003 | Momin et al. |
| 8,092,813 B1 * | 1/2012 | Novicki ............... 424/278.1 |

OTHER PUBLICATIONS

Akutsu, et al., "Occurrence of polybrominated diphenyl ethers and polychlorinated biphenyls in shark liver oil supplements," Food Addit Contam 23:1323-1329 (2006).
Derek O'Hagan, "MF59 is a Safe and Potent Vaccine Adjuvant That Enhances Protection Against Influenza Virus Infection", Expert Rev., Vaccines 6(5):699-710 (2007).
Heilmann, et al., "Reduced antibody responses to vaccinations in children exposed to polychlorinated biphenyls," PLoS Med 3(8):e311 (2006).
Podda, "The adjuvanted influenza vaccines with novel adjuvants: experience with the MF59—adjuvanted vaccine," Vaccine 19:2673-2680 (2001).
Storelli, et al., "Concentrations and hazard assessment of polychlorinated biphenyls and organochlorine pesticides in shark liver from the Mediterranean Sea," Mar Mollut Bull 50:850-855 (2005).
Schultze et al., "Safety of MF59 Adjuvant", Vaccine 26:3209-3222 (2008).
Undesirable Substances in Seafood Products—Results From the Monitoring Activities in 2004. Icelandic Fisheries Laboratories Report 33-05.

* cited by examiner

*Primary Examiner* — Yunsoo Kim
(74) *Attorney, Agent, or Firm* — Regina Bautista

(57) ABSTRACT

When using squalene in a vaccine adjuvant, there is a possibility of contamination with polychlorinated biphenyls (PCBs). Environmental exposure to PCBs may adversely affect children's immune responses to routine vaccinations. Thus the invention uses squalene with low or no PCB contamination, particularly when derived from shark liver.

27 Claims, No Drawings

POLYCHLORINATED BIPHENYLS AND SQUALENE-CONTAINING ADJUVANTS

CROSS-REFERENCE TO RELATED APPLICATIONS

This application is a continuation of U.S. patent application Ser. No. 12/287,891, filed Oct. 14, 2008, now U.S. Pat. No. 8,092,813, from which application priority is claimed pursuant to 35 U.S.C. §120, which claims the benefit under 35 U.S.C. §119(e)(1) of U.S. Provisional Application No. 61/009,425 filed Dec. 28, 2007, which applications are incorporated herein by reference in their entireties.

TECHNICAL FIELD

This invention is in the field of vaccine adjuvant manufacture and, in particular, the avoidance of contamination in squalene-containing adjuvants.

BACKGROUND ART

Reference 1 reports that environmental exposure to polychlorinated biphenyls (PCBs) may adversely affect children's immune responses to routine vaccinations.

DISCLOSURE OF THE INVENTION

The vaccine adjuvant known as 'MF59' [2-4] is a submicron oil-in-water emulsion of squalene, Tween 80, and Span 85. Other squalene-based emulsion adjuvants are also known.

The commercial source of squalene is typically shark liver oil, and the inventor has found that PCBs can be present at high levels even in pharmaceutical-quality squalene from commercial suppliers. If parenterally-administered PCBs have the same negative immunological effect as environmental PCBs then an adjuvant containing PCB-contaminated squalene may inhibit rather than enhance the efficacy of a vaccine. To reduce this iatrogenic risk, the invention uses squalene with low or no PCB contamination. A maximum level of 661 picograms of PCBs per gram of squalene (TEQ) has been determined by the inventor, but much lower levels can be achieved.

Thus the invention provides an oil-in-water emulsion adjuvant comprising squalene, wherein the emulsion contains less than 661 picograms of PCBs per gram of squalene (TEQ).

These adjuvants may be combined with antigens to give vaccine compositions. Thus the invention also provides a vaccine composition comprising an antigen and an oil-in-water emulsion, wherein the vaccine comprises squalene and contains less than 661 picograms of PCBs per gram of squalene (TEQ).

The invention provides a process for preparing an oil-in-water emulsion, comprising steps of: mixing an oil component and an aqueous component, wherein the oil component comprises squalene and has less than 661 picograms of PCBs per gram of squalene (TEQ). The process may involve mixing the oil and aqueous components with a surfactant. The mixing may involve microfluidisation e.g. to provide an emulsion with submicron droplets.

The invention also provides a process for preparing a vaccine, comprising steps of: mixing an oil component, an aqueous component and an antigen, wherein the oil component comprises squalene and has less than 661 picograms of PCBs per gram of squalene (TEQ). As described above, the process may also involve mixing with a surfactant and/or microfluidisation.

The invention also provides an oil-in-water emulsion adjuvant comprising squalene, wherein the emulsion contains no 3',4,4',5,5'-hexachlorobiphenyl. This PCB is IUPAC #169. The invention also provides a vaccine composition comprising an antigen and an oil-in-water emulsion, wherein the vaccine comprises squalene but no 3',4,4',5,5'-hexachlorobiphenyl.

The invention also provides a process for preparing an oil-in-water emulsion, comprising steps of: mixing an oil component and an aqueous component, wherein the oil component comprises squalene but no 3',4,4',5,5'-hexachlorobiphenyl. The process may involve mixing the oil and aqueous components with a surfactant. The mixing may involve microfluidisation.

The invention also provides a process for preparing a vaccine, comprising steps of: mixing an oil component, an aqueous component and an antigen, wherein the oil component comprises squalene but no 3',4,4',5,5'-hexachlorobiphenyl. As described above, the process may also involve mixing with a surfactant and/or microfluidisation.

The invention also provides an oil-in-water emulsion adjuvant comprising squalene, wherein the emulsion contains no 3,3',4,4',5-pentachlorobiphenyl. This PCB is IUPAC #126. The invention also provides a vaccine composition comprising an antigen and an oil-in-water emulsion, wherein the vaccine comprises squalene but no 3,3',4,4',5-pentachlorobiphenyl.

The invention also provides a process for preparing an oil-in-water emulsion, comprising steps of: mixing an oil component and an aqueous component, wherein the oil component comprises squalene but no 3,3',4,4',5-pentachlorobiphenyl. The process may involve mixing the oil and aqueous components with a surfactant. The mixing may involve microfluidisation.

The invention also provides a process for preparing a vaccine, comprising steps of: mixing an oil component, an aqueous component and an antigen, wherein the oil component comprises squalene but no 3,3',4,4',5-pentachlorobiphenyl. As described above, the process may also involve mixing with a surfactant and/or microfluidisation.

The invention also provides an oil-in-water emulsion adjuvant comprising squalene, wherein the emulsion contains no 3,3',4,4'-tetrachlorobiphenyl. This PCB is IUPAC #77. The invention also provides a vaccine composition comprising an antigen and an oil-in-water emulsion, wherein the vaccine comprises squalene but no 3,3',4,4'-tetrachlorobiphenyl.

The invention also provides a process for preparing an oil-in-water emulsion, comprising steps of: mixing an oil component and an aqueous component, wherein the oil component comprises squalene but no 3,3',4,4'-tetrachlorobiphenyl. The process may involve mixing the oil and aqueous components with a surfactant. The mixing may involve microfluidisation.

The invention also provides a process for preparing a vaccine, comprising steps of mixing an oil component, an aqueous component and an antigen, wherein the oil component comprises squalene but no 3,3',4,4'-tetrachlorobiphenyl. As described above, the process may also involve mixing with a surfactant and/or microfluidisation.

The invention also provides an oil-in-water emulsion adjuvant comprising squalene, wherein the emulsion contains no 3,4,4',5-tetrachlorobiphenyl. This PCB is IUPAC #81. The invention also provides a vaccine composition comprising an antigen and an oil-in-water emulsion, wherein the vaccine comprises squalene but no 3,4,4',5-tetrachlorobiphenyl.

The invention also provides a process for preparing an oil-in-water emulsion, comprising steps of: mixing an oil component and an aqueous component, wherein the oil component comprises squalene but no 3,4,4',5-tetrachlorobiphenyl. The process may involve mixing the oil and aqueous components with a surfactant. The mixing may involve microfluidisation.

The invention also provides a process for preparing a vaccine, comprising steps of: mixing an oil component, an aqueous component and an antigen, wherein the oil component comprises squalene but no 3,4,4',5-tetrachlorobiphenyl. As described above, the process may also involve mixing with a surfactant and/or microfluidisation.

The invention also provides a process for preparing a vaccine, comprising a step of combining an emulsion of the invention with an antigen.

The invention also provides a process for preparing a vaccine, comprising steps of: (i) preparing an emulsion as described above; and (ii) combining this emulsion with an antigen.

The invention also provides a process for preparing a vaccine, comprising steps of: (i) preparing an emulsion as described above; and (ii) packaging the emulsion into a kit as a kit component together with an antigen component. The antigen and emulsion kit components can then be combined at a later time (e.g. at the point of use) for administration to a patient.

In these processes of the invention, the oil component preferably comprises shark-derived squalene. Any suitable shark species can be used, such as the spiny dogfish (*Squalus acanthias*). Other suitable species include *Centrophorus atromarginatus, Cetorhinus maximus, Echinorhinus brucus, Scymnodon squamulosus, Centrophorus atromarginatus, Etmopterus frontimaculatus, Deania eglantina* and *Scymnodon foliaceus*.

Squalene and PCBs

Compositions of the invention include squalene, an unsaturated terpenoid oil 2,6,10,15,19,23-hexamethyl-2,6,10,14,18,22-tetracosahexaene (formula [(CH$_3$)$_2$C[=CHCH$_2$CH$_2$C(CH$_3$)]$_2$=CHCH$_2$—]$_2$; CAS RN 7683-64-9). Ideally it is at least 95% in its trans-configuration (natural isomer; 'E,E,E,E squalene' or all-E squalene') e.g. >96%, >97%, >98%, >99%, or even 100%.

The squalene used with the invention will typically be shark-derived (usually from the liver). Reference 5 found PCB levels in blue shark (*Prionace glauca*) liver of 2482 ng/g and in kitefin shark (*Dalatias licha*) liver of 1824 ng/g, with both sources showing a bias towards higher chlorinated congeners (e.g. >60% hexachlorobiphenyls). PCB levels can vary widely in commercial shark-derived oils, including in squalene. For example, reference 6 reported that PCB levels in different dietary supplements can vary >20-fold, and the authors found PCB levels as high as 340 ng/g in two Japanese brands of shark liver oil. Even higher levels have been reported e.g. reference 7 measured 1060 ng/g in a dietary squalene product. The manufacturer of the shark-derived dietary supplement known as "Good Health squalene" reports PCB levels in its product of ≤50 ppb (i.e. <50 ng/g). The same PCB levels are reported for SeaDragon's "Balanced Deep Sea Shark Liver Oils".

According to the invention, PCBs are present at a level of less than 661 pg PCBs per g squalene (TEQ). This 661 pg/g limit can be applied to the squalene used to make an emulsion, the final emulsion, and to a vaccine made using the emulsion. Usually it applies to the squalene used to make an emulsion.

When using shark-derived squalene, the 661 pg/g threshold can be achieved in various ways. One way is to remove PCBs by a purification process. A simpler method involves selection and/or rejection of certain squalene supplies e.g. to select only squalene derived from sharks that have lived in waters having low PCB contamination levels. Thus the PCB content of a squalene material can be measured, and material with too much PCB can be rejected for further use.

Sensitive quantitative assays for PCBs are well known in the art, particularly from the toxicology field. For instance, reference 8 describes the use of gas chromatographic columns for monitoring PCBs, and reports that solid phase microextraction methods have a minimum extraction limit of less than 5 parts per trillion (ppt). The ELISA kit from Abraxis LLC (Warminster, Pa.) has an assay range between 25 ppt and 1000 ppt [9]. The International Fish Oil Standards Program measures PCB levels using liquid chromatography mass spectrometry at a ppt detection limit. Appendix F of reference 10 discusses the use of GC-MS (gas chromatography, mass spectrometry) and GC-ECD (gas chromatography, electron capture detection) techniques with detection limits in the lower ppb to ppt. A variety of assays are therefore available for accurately measuring low levels of PCBs.

PCBs are a family of chemical compounds formed by the addition of chlorine to biphenyl. The biphenyl ring means that there are 10 possible positions for chlorine substitution:

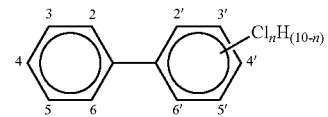

Any single chemical compound in the PCB category is called a "congener". There are 209 PCB congeners. Rather than assay each of these 209, PCB assays typically look at the sum of levels of a subset of congeners. A standard subset is the "ICES7" or "Dutch 7", made up of the seven PCBs with IUPAC numbers 28, 52, 101, 118, 138, 153 and 180. Another subset that is used is the mono-ortho substituted PCBs (105, 114, 118, 123, 156, 157, 167, 189). Another subset that is used is the twelve dioxin-like PCBs (non-ortho 77, 81, 126, 169; mono-ortho 105, 114, 118, 123, 156, 157, 167, 189), optionally augmented by congeners 170 and 180.

Where multiple congeners are examined then, regardless of the actual number, according to the invention the levels are converted to a toxic equivalent (TEQ). TEQs allow the toxicity of a mixture of PCBs to be represented as a single number. The toxicity of each PCB is expressed as a fraction (the toxic equivalency factor, TEF) of the toxicity of 2,3,7,8-TCDD dioxin (which has a reference value of 1). To calculate the total TEQ of a mixture, the mass of each PCB is multiplied by its TEF and then the TEQ is the sum of these values. Table I lists WHO 2005 TEF values for PCBs in humans, and these TEFs are used to calculate TEQs according to the invention. In some embodiments of the invention, TEQ may be based on the twelve dioxin-like PCBs (Table I); in other embodiments, TEQ may be based on a 14-PCB combination of the twelve dioxin-like PCBs, IUPAC congener #170 (TEF 0.0001) and IUPAC congener #180 (TEF 0.00001).

As an alternative to purifying or selecting an appropriate shark-derived squalene, a non-shark source may be used. For instance, squalene can be purified from olive oil (e.g. see ref. 11). Further sources include wheat germ oil, palm oil, amaranth seed (e.g. see ref. 12), and rice bran oil. Squalene can also be purified from some yeasts, but in some embodiments of this invention a yeast source is not preferred. Even with these sources, however, the 661 pg/g threshold must be satisfied.

The inventors have found that much lower levels than 661 pg/g can be achieved, even using shark-derived squalene. The inventors routinely use squalene with PCB levels as low as ~2 picograms per gram squalene. The maximum PCB content in compositions of the invention may thus be selected from 600, 500, 402, 400, 300, 200, 100, 90, 80, 70, 60, 50, 40, 35, 30, 20, 10, 9, 8, 7, 6, 5, 4, 3, 2, or 1 pg of PCB per g of squalene (TEQ).

In some embodiments the squalene has, in addition to a TEQ as above, no detectable PCB #126.

In some embodiments the squalene has, in addition to a TEQ as above, no detectable PCB #169.

In some embodiments the squalene has, in addition to a TEQ as above, no detectable PCB #77.

In some embodiments the squalene has, in addition to a TEQ as above, no detectable PCB #81.

In some embodiments the squalene has, in addition to a TEQ as above, no detectable PCB #123.

In some embodiments the squalene has, in addition to a TEQ as above, <20 ng/g of PCB #170.

In some embodiments the squalene has, in addition to a TEQ as above, <45 ng/g of PCB #180.

As well as having a low PCB content, it is useful to ensure low dioxin levels. Thus each of the following may have a low dioxin content: squalene used to form emulsions; the final emulsion; and a vaccine made using the emulsion. A low dioxin content is less than 1 ng per gram of squalene, and preferably less than 1 pg/g (TEQ).

The invention provides an oil-in-water emulsion adjuvant comprising squalene, wherein the emulsion contains less than 1 nanogram of dioxins per gram of squalene. The invention also provides a vaccine composition comprising an antigen and an oil-in-water emulsion, wherein the vaccine comprises squalene and contains less than 1 nanogram of dioxins per gram of squalene. The invention also provides a process for preparing an oil-in-water emulsion, comprising steps of: mixing an oil component and an aqueous component, wherein the oil component comprises squalene and has less than 1 nanogram of dioxins per gram of squalene. The invention also provides a process for preparing a vaccine, comprising steps of mixing an oil component, an aqueous component and an antigen, wherein the oil component comprises squalene and has less than 1 nanogram of dioxins per gram of squalene. Further details are as described elsewhere herein.

Similarly it is useful to ensure low furan levels. Thus each of the following may have a low furan content: squalene used to form emulsions; the final emulsion; and a vaccine made using the emulsion. A low furan content is less than 1 ng per gram of squalene, and preferably <1 pg/g (TEQ).

The invention provides an oil-in-water emulsion adjuvant comprising squalene, wherein the emulsion contains less than 1 nanogram of furans per gram of squalene. The invention also provides a vaccine composition comprising an antigen and an oil-in-water emulsion, wherein the vaccine comprises squalene and contains less than 1 nanogram of furans per gram of squalene. The invention also provides a process for preparing an oil-in-water emulsion, comprising steps of: mixing an oil component and an aqueous component, wherein the oil component comprises squalene and has less than 1 nanogram of furans per gram of squalene. The invention also provides a process for preparing a vaccine, comprising steps of: mixing an oil component, an aqueous component and an antigen, wherein the oil component comprises squalene and has less than 1 nanogram of furans per gram of squalene. Further details are as described elsewhere herein.

Emulsions

Compositions of the invention are based on oil-in-water emulsions. The oil in the emulsion comprises squalene. In addition to squalene (and, optionally, one or more further other oils), the emulsion includes an aqueous phase. Also, it will normally include one or more surfactant(s).

In addition to squalene, emulsions may additionally include one or more further oil(s). Any such further oils are preferably biodegradable (metabolisable) and biocompatible. Additional oils include those from an animal (such as fish) or vegetable source. Sources for vegetable oils include nuts, seeds and grains. Peanut oil, soybean oil, coconut oil, and olive oil, the most commonly available, exemplify the nut oils. Jojoba oil can be used e.g. obtained from the jojoba bean. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used. 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk are metabolizable and may therefore be used in the practice of this invention. The procedures for separation, purification, saponification and other means necessary for obtaining pure oils from animal sources are well known in the art. Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids, which include squalene. Squalane, the saturated analog to squalene, can also be used. Fish oils, including squalene and squalane, are readily available from commercial sources or may be obtained by methods known in the art. Other preferred oils are the tocopherols. Where a composition includes a tocopherol, any of the $\alpha$, $\beta$, $\gamma$, $\delta$, $\epsilon$ or $\xi$ tocopherols can be used, but $\alpha$-tocopherols are preferred. The tocopherol can take several forms e.g. different salts and/or isomers. Salts include organic salts, such as succinate, acetate, nicotinate, etc. D-$\alpha$-tocopherol and DL-$\alpha$-tocopherol can both be used. A preferred $\alpha$-tocopherol is DL-$\alpha$-tocopherol. If a salt of this tocopherol is to be used, the preferred salt is the succinate. Where an $\alpha$-tocopherol is used, a weight excess of tocopherol may be used.

Total oil content may be up to about 20% by volume e.g. between 5-15% e.g. about 10%.

If oils are used in addition to squalene, they may contribute PCB contamination of their own. Overall, however, the PCB content must be kept below 661 pg per gram of squalene.

The aqueous phase of the emulsion is preferably buffered e.g. phosphate buffered saline. Any materials used to form the aqueous phase may contribute PCB contamination of their own. Overall, however, the PCB content must be kept below 661 pg per gram of squalene.

Surfactants used with the invention are preferably biodegradable (metabolisable) and biocompatible. Surfactants can be classified by their 'HLB' (hydrophile/lipophile balance). Preferred surfactants of the invention have a HLB of at least 10, preferably at least 15, and more preferably at least 16. The invention can be used with surfactants including, but not limited to: the polyoxyethylene sorbitan esters surfactants (commonly referred to as the Tweens), especially polysorbate 20 and polysorbate 80; copolymers of ethylene oxide (EO), propylene oxide (PO), and/or butylene oxide (BO), sold under the DOWFAX™ tradename, such as linear BO/PO block copolymers; octoxynols, which can vary in the number of repeating ethoxy (oxy-1,2-ethanediyl) groups, with octoxynol-9 (Triton X-100, or t-octylphenoxypolyethoxyethanol)

being of particular interest; (octylphenoxy)polyethoxyethanol (IGEPAL CA-630/NP-40); phospholipids such as phosphatidylcholine (lecithin); polyoxyethylene fatty ethers derived from lauryl, cetyl, stearyl and oleyl alcohols (known as Brij surfactants), such as triethyleneglycol monolauryl ether (Brij 30); polyoxyethylene-9-lauryl ether; and sorbitan esters (commonly known as the Span series), such as sorbitan trioleate (Span 85) and sorbitan monolaurate. Preferred surfactants for including in the emulsion are Tween 80 (polyoxyethylene sorbitan monooleate; polysorbate 80), Span 85 (sorbitan trioleate), lecithin and Triton X-100. Mixtures of surfactants can be used e.g. Tween 80/Span 85 mixtures, or Tween80/Triton-X100 mixtures. If only one surfactant is present in the emulsion, it is preferably Tween 80; if only two surfactants are present in the emulsion, they are preferably Tween 80 and Span 85.

Typical amounts of surfactants (% by weight) are: polyoxyethylene sorbitan esters (such as Tween 80) 0.01 to 1%, in particular about 0.1%; octyl- or nonylphenoxy polyoxyethanols (such as Triton X-100, or other detergents in the Triton series) 0.001 to 0.1%, in particular 0.005 to 0.02%; polyoxyethylene ethers (such as laureth 9) 0.1 to 20%, preferably 0.1 to 10% and in particular 0.1 to 1% or about 0.5%.

Specific oil-in-water emulsion adjuvants that can be used with the invention include, but are not limited to:

A submicron emulsion of squalene, Tween 80, and Span 85. The composition of the emulsion by volume can be about 5% squalene, about 0.5% polysorbate 80 and about 0.5% Span 85. In weight terms, these amounts become 4.3% squalene, 0.5% polysorbate 80 and 0.48% Span 85. This adjuvant is known as 'MF59' and is described in more detail in Chapter 10 of ref. 13 and chapter 12 of ref. 14. The oil droplets in MF59 are small enough to be sterile-filtered through a 0.2 µm filter. The MF59 emulsion advantageously includes citrate ions e.g. 10 mM sodium citrate buffer.

An emulsion (preferably with submicron droplets) of squalene, a tocopherol, and Tween 80. The emulsion may include phosphate buffered saline. It may also include Span 85 (e.g. at 1%) and/or lecithin. These emulsions may have from 2 to 10% squalene, from 2 to 10% tocopherol and from 0.3 to 3% Tween 80, and the weight ratio of squalene:tocopherol is preferably ≤1 (e.g. 0.90) as this can provide a more stable emulsion. Squalene and Tween 80 may be present volume ratio of about 5:2 or at a weight ratio of about 11:5. One such emulsion can be made by dissolving Tween 80 in PBS to give a 2% solution, then mixing 90 ml of this solution with a mixture of (5 g of DL-α-tocopherol and 5 ml squalene), then microfluidising the mixture. A squalene:tocpherol:Tween 80 weight ratio of 40-45:45-50:15-25 is preferred e.g. 43±1:48±1:20±1, or 43:48:20. The resulting emulsion may have submicron oil droplets e.g. with an average diameter of between 100 and 250 nm, preferably about 180 nm. The emulsion may also include a 3-de-O-acylated monophosphoryl lipid A (3d-MPL). Another useful emulsion of this type may comprise, per human dose, 0.5-10 mg squalene, 0.5-11 mg tocopherol, and 0.1-4 mg polysorbate 80 [15].

An emulsion of squalene, a tocopherol, and a Triton detergent (e.g. Triton X-100). The emulsion may also include a 3-O-deacylated monophosphoryl lipid A ('3d-MPL'). The emulsion may contain a phosphate buffer.

An emulsion of squalene, polysorbate 80 and poloxamer 401 ("Pluronic™ L121"). The emulsion can be formulated in phosphate buffered saline, pH 7.4. This emulsion is a useful delivery vehicle for muramyl dipeptides. Microfluidisation is preferred.

An emulsion comprising squalene, an aqueous solvent, a polyoxyethylene alkyl ether hydrophilic nonionic surfactant (e.g. polyoxyethylene (12) cetostearyl ether) and a hydrophobic nonionic surfactant (e.g. a sorbitan ester or mannide ester, such as sorbitan monoleate or 'Span 80'). The emulsion is preferably thermoreversible and/or has at least 90% of the oil droplets (by volume) with a size less than 200 nm [16]. The emulsion may also include one or more of: alditol; a cryoprotective agent (e.g. a sugar, such as dodecylmaltoside and/or sucrose); and/or an alkylpolyglycoside. The emulsion may include a TLR4 agonist [17]. Such emulsions may be lyophilized.

An emulsion of squalene, poloxamer 105 and Abil-Care [18]. The final concentration (weight) of these components in adjuvanted vaccines are 5% squalene, 4% poloxamer 105 (pluronic polyol) and 2% Abil-Care 85 (Bis-PEG/PPG-16/16 PEG/PPG-16/16 dimethicone; caprylic/capric triglyceride).

An emulsion in which a saponin (e.g. QuilA or QS21) and a sterol (e.g. a cholesterol) are associated as helical micelles [19], together with squalene.

Substantially all (e.g. >95% by number, or >99% by number) of the oil droplets in the emulsion are typically less than 1 µm in diameter (on average), and may be smaller e.g. <500 nm, <250 nm. Sub-micron diameters can easily be achieved with a microfluidiser to provide stable emulsions. Droplets with a size less than 220 nm are particularly preferred, as they can be subjected to filter sterilization.

The Vaccine

Although it is possible to administer oil-in-water emulsion adjuvants on their own to patients (e.g. to provide an adjuvant effect for an antigen that has been separately administered to the patient), it is more usual to admix the adjuvant with an antigen prior to administration. This admixing may take place during manufacture, such that the distributed vaccine product is ready for administration, or can take place at the time of use. Thus emulsion adjuvants of the invention can be used to manufacture vaccines.

Mixing will usually involve combining the emulsion with an aqueous preparation of antigen. Where mixing of antigen and adjuvant takes place during manufacture then the volumes of bulk antigen and adjuvant that are mixed will typically be greater than 1 liter e.g. ≥5 liters, ≥10 liters, ≥20 liters, ≥50 liters, etc. Where mixing takes place at the point of use, however, then the volumes that are mixed will typically be smaller than 1 milliliter e.g. ≤0.6 ml, ≤0.5 ml, ≤0.4 ml, ≤0.3 ml, ≤0.2 ml, etc. In both cases it is usual for substantially equal volumes of emulsion and antigen solution to be mixed i.e. substantially 1:1 (e.g. between 1.1:1 and 1:1.1, preferably between 1.05:1 and 1:1.05, and more preferably between 1.025:1 and 1:1.025). In some embodiments, however, an excess of adjuvant or an excess of antigen may be used. Where an excess volume of one component is used, the excess will generally be at least 1.5:1 e.g. ≥2:1, ≥2.5:1, ≥3:1, ≥4:1, ≥5:1, etc.

Before admixing, the squalene-containing emulsion contains less than 661 picograms of PCBs per gram of squalene (TEQ). After admixing, the vaccine preferably contains less than 661 picograms of PCBs per gram of squalene (TEQ). Preferred antigen components mixed with the emulsions are substantially free from PCBs.

Antigen and adjuvant may be presented as separate components within a kit. In this arrangement they are physically separate from each other within the kit, and this separation can be achieved in various ways. For instance, the components may be in separate containers, such as vials. The contents of two vials can then be mixed when needed e.g. by removing the contents of one vial and adding them to the other vial, or by separately removing the contents of both vials and mixing them in a third container.

In one arrangement, one of the kit components is in a syringe and the other is in a container such as a vial. The syringe can be used (e.g. with a needle) to insert its contents into the second container for mixing, and the mixture can then be withdrawn into the syringe. The mixed contents of the syringe can then be administered to a patient, typically through a new sterile needle. Packing one component in a syringe eliminates the need for using a separate syringe for patient administration.

In another arrangement, the two kit components are held together but separately in the same syringe e.g. a dual-chamber syringe, such as those disclosed in references 20-27 etc. When the syringe is actuated (e.g. during administration to a patient) then the contents of the two chambers are mixed. This arrangement avoids the need for a separate mixing step at the time of use.

As mentioned above, the contents of the various kit components will generally all be in aqueous form. In some arrangements, however, a component (typically the antigen component rather than the emulsion component) is in dry form (e.g. in a lyophilised form), with the other component being in aqueous form. The two components can be mixed in order to reactivate the dry component and give an aqueous composition for administration to a patient. A lyophilised component will typically be located within a vial rather than a syringe. Dried components may include stabilizers such as lactose, sucrose or mannitol, as well as mixtures thereof e.g. lactose/sucrose mixtures, sucrose/mannitol mixtures, etc. One possible arrangement uses an aqueous emulsion component in a pre-filled syringe and a lyophilised antigen component in a vial.

If kits contain components in addition to the adjuvant and the antigen then these further components may be included in one these two kit components, or may be part of a third kit component.

Suitable containers for mixed vaccines of the invention, or for individual kit components, include vials and disposable syringes. These containers should be sterile.

Where a composition/component is located in a vial, the vial is preferably made of a glass or plastic material. The vial is preferably sterilized before the composition is added to it. To avoid problems with latex-sensitive patients, vials are preferably sealed with a latex-free stopper, and the absence of latex in all packaging material is preferred. The vial may include a single dose of vaccine, or it may include more than one dose (a 'multidose' vial) e.g. 10 doses. Preferred vials are made of colorless glass.

A vial can have a cap (e.g. a Luer lock) adapted such that a pre-filled syringe can be inserted into the cap, the contents of the syringe can be expelled into the vial (e.g. to reconstitute lyophilised material therein), and the contents of the vial can be removed back into the syringe. After removal of the syringe from the vial, a needle can then be attached and the composition can be administered to a patient. The cap is preferably located inside a seal or cover, such that the seal or cover has to be removed before the cap can be accessed. A vial may have a cap that permits aseptic removal of its contents, particularly for multidose vials.

Where a composition/component is packaged into a syringe, the syringe may have a needle attached to it. If a needle is not attached, a separate needle may be supplied with the syringe for assembly and use. Such a needle may be sheathed. Safety needles are preferred. 1-inch 23-gauge, 1-inch 25-gauge and ⅝-inch 25-gauge needles are typical. Syringes may be provided with peel-off labels on which the lot number and expiration date of the contents may be printed, to facilitate record keeping. The plunger in the syringe preferably has a stopper to prevent the plunger from being accidentally removed during aspiration. The syringes may have a latex rubber cap and/or plunger. Disposable syringes contain a single dose of vaccine. The syringe will generally have a tip cap to seal the tip prior to attachment of a needle, and the tip cap is preferably made of a butyl rubber. If the syringe and needle are packaged separately then the needle is preferably fitted with a butyl rubber shield. Useful syringes are those marketed under the trade name "Tip-Lok"™.

Containers may be marked to show a half-dose volume e.g. to facilitate delivery to children. For instance, a syringe containing a 0.5 ml dose may have a mark showing a 0.25 ml volume.

Where a glass container (e.g. a syringe or a vial) is used, then it is preferred to use a container made from a borosilicate glass rather than from a soda lime glass.

A kit or composition may be packaged (e.g. in the same box) with a leaflet including details of the vaccine e.g. instructions for administration, details of the antigens within the vaccine, etc. The instructions may also contain warnings e.g. to keep a solution of adrenaline readily available in case of anaphylactic reaction following vaccination, etc.

Vaccine Immunogens

Vaccine compositions will include antigens. Various antigens can be used with oil-in-water emulsions, including but not limited to: viral antigens, such as viral surface proteins; bacterial antigens, such as protein and/or saccharide antigens; fungal antigens; parasite antigens; and tumor antigens. The invention is particularly useful for pediatric vaccines (cf. ref. 1).

The invention is particularly useful for vaccines against influenza virus, HIV, hookworm, hepatitis B virus, herpes simplex virus, rabies, respiratory syncytial virus, cytomegalovirus, *Staphylococcus aureus*, chlamydia, SARS coronavirus, varicella zoster virus, *Streptococcus pneumoniae, Mycobacterium tuberculosis, Bacillus anthracis, Neisseria meningitidis*, Epstein Barr virus, human papillomavirus, etc.

Influenza virus antigens. These may take the form of a live virus or an inactivated virus. Where an inactivated virus is used, the vaccine may comprise whole virion, split virion, or purified surface antigens (including hemagglutinin and, usually, also including neuraminidase). Influenza antigens can also be presented in the form of virosomes [28]. The antigens may have any hemagglutinin subtype, selected from H1, H2, H3, H4, H5, H6, H7, H8, H9, H10, H11, H12, H13, H14, H15 and/or H16. The antigens may have any neuraminidase subtype, selected from N1, N2, N3, N4, N5, N6, N7, N8 or N9. Vaccine may include antigen(s) from one or more (e.g. 1, 2, 3, 4 or more) influenza virus strains, including influenza A virus and/or influenza B virus. The influenza virus may be a reassortant strain, and may have been obtained by reverse genetics techniques [e.g. 29-33]. Thus the virus may include one or more RNA segments from a A/PR/8/34 virus (typically 6 segments from A/PR/8/34, with the HA and N segments being from a vaccine strain, i.e. a 6:2 reassortant). The viruses used as the source of the antigens can be grown either on eggs (e.g. embryonated hen eggs) or on cell culture. Where cell culture is used, the cell substrate will typically be a mammalian cell line, such as MDCK; CHO; 293T;

BHK; Vero; MRC-5; PER.C6; WI-38; etc. Preferred mammalian cell lines for growing influenza viruses include: MDCK cells [34-37], derived from Madin Darby canine kidney; Vero cells [38-40], derived from African green monkey (*Cercopithecus aethiops*) kidney; or PER.C6 cells [41], derived from human embryonic retinoblasts. These cell lines are widely available e.g. from the American Type Cell Culture (ATCC) collection [42], from the Coriell Cell Repositories [43], or from the European Collection of Cell Cultures (ECACC). For example, the ATCC supplies various different Vero cells under catalog numbers CCL-81, CCL-81.2, CRL-1586 and CRL-1587, and it supplies MDCK cells under catalog number CCL-34. PER.C6 is available from the ECACC under deposit number 96022940. As a less-preferred alternative to mammalian cell lines, virus can be grown on avian cell lines [e.g. refs. 44-46], including cell lines derived from ducks (e.g. duck retina) or hens e.g. chicken embryo fibroblasts (CEF), etc. Where virus has been grown on a mammalian cell line then the composition will advantageously be free from egg proteins (e.g. ovalbumin and ovomucoid) and from chicken DNA, thereby reducing allergenicity.

Human immunodeficiency virus, including HIV-1 and HIV-2. The antigen will typically be an envelope antigen.

Hepatitis B virus surface antigens. This antigen is preferably obtained by recombinant DNA methods e.g. after expression in a *Saccharomyces cerevisiae* yeast. Unlike native viral HBsAg, the recombinant yeast-expressed antigen is non-glycosylated. It can be in the form of substantially-spherical particles (average diameter of about 20 nm), including a lipid matrix comprising phospholipids. Unlike native HBsAg particles, the yeast-expressed particles may include phosphatidylinositol. The HBsAg may be from any of subtypes ayw1, ayw2, ayw3, ayw4, ayr, adw2, adw4, adrq− and adrq+.

Hepatitis C virus surface antigens [47]. Hepatitis C virus antigens that may be used can include one or more of the following: HCV E1 and or E2 proteins, E1/E2 heterodimer complexes, core proteins and non-structural proteins, or fragments of these antigens. Such proteins may be modified to remove enzymatic activity but retain immunogenicity (e.g. refs. 48-50).

Hookworm, particularly as seen in canines (*Ancylostoma caninum*). This antigen may be recombinant Ac-MTP-1 (astacin-like metalloprotease) and/or an aspartic hemoglobinase (Ac-APR-1), which may be expressed in a baculovirus/insect cell system as a secreted protein [51, 52].

Herpes simplex virus antigens (HSV). A preferred HSV antigen for use with the invention is membrane glycoprotein gD. It is preferred to use gD from a HSV-2 strain ('gD2' antigen). The composition can use a form of gD in which the C-terminal membrane anchor region has been deleted [53] e.g. a truncated gD comprising amino acids 1-306 of the natural protein with the addition of aparagine and glutamine at the C-terminus. This form of the protein includes the signal peptide which is cleaved to yield a mature 283 amino acid protein. Deletion of the anchor allows the protein to be prepared in soluble form.

Human papillomavirus antigens (HPV). Preferred HPV antigens for use with the invention are L1 capsid proteins, which can assemble to form structures known as virus-like particles (VLPs). The VLPs can be produced by recombinant expression of L1 in yeast cells (e.g. in *S. cerevisiae*) or in insect cells (e.g. in *Spodoptera* cells, such as *S. frugiperda*, or in *Drosophila* cells). For yeast cells, plasmid vectors can carry the L1 gene(s); for insect cells, baculovirus vectors can carry the L1 gene(s). More preferably, the composition includes L1 VLPs from both HPV-16 and HPV-18 strains. This bivalent combination has been shown to be highly effective [54]. In addition to HPV-16 and HPV-18 strains, it is also possible to include L1 VLPs from HPV-6 and HPV-11 strains. The use of oncogenic HPV strains is also possible. A vaccine may include between 20-60 μg/ml (e.g. about 40 μg/ml) of L1 per HPV strain.

Anthrax antigens. Anthrax is caused by *Bacillus anthracis*. Suitable *B. anthracis* antigens include A-components (lethal factor (LF) and edema factor (EF)), both of which can share a common B-component known as protective antigen (PA). The antigens may optionally be detoxified. Further details can be found in references 55 to 57.

*Helicobacter pylori* antigens. *H. pylori* can cause gastritis, peptic ulcer disease, gastric adenocarcinoma and gastric B cell lymphoma. Vaccines may contain *H. pylori* antigens such as CagA [58-61], VacA [62,63], NAP [64-66], HopX [67], HopY [67] and/or urease.

Meningococcal antigens. *Neisseria meningitidis* is a cause of bacterial meningitis. Suitable meningococcal antigens include conjugated capsular saccharides (particularly for serogroups A, C, W135 and Y), recombinant proteins (e.g. GNA1870) and/or outer membrane vesicles.

Cancer antigens. A variety of tumour-specific antigens are known. The invention may be used with antigens that elicit an immunotherapeutic response against lung cancer, melanoma, breast cancer, prostate cancer, etc.

The invention is also useful with antigens based on hybrid or fusion proteins that comprise a viral surface antigen and a heterologous antigen. For instance, it is known to fuse the HBsAg sequence to heterologous antigens to exploit HBsAg's ability to assemble into particles. For example, reference 68 reports fusions of HIV-1 gp120 to HBsAg to give a protein that spontaneously assembled into particles that resemble native HBsAg particles. This approach has also been used for malaria vaccines. Reference 69 reports that epitopes of up to 61aa from the malaria gp190 antigen were inserted into the HBsAg sequence, and that the expressed hybrid particles could elicit an anti-gp190 immune response in animals. Reference 70 report an protein having 16 repeats of a 4-mer sequence of the circumsporozoite protein expressed as a fusion protein with HBsAg. Reference 71 reports the production in yeast of virus-like particles composed of Pfs 16 fused to HBsAg. Reference 72 discloses a hybrid antigen in which the circumsporozoite protein is fused to HBsAg. Reference 73 discloses a fusion of the C-terminal region of the merozoite surface 1 protein of *P. vivax*, which formed immunogenic particles of 20-45 nm size. The use of HBsAg for presenting malarial antigens in self-assembling particulate form is therefore well known in the art. Thus the invention can be used with hybrid antigens that comprise a viral surface antigen and a heterologous antigen. Particularly where the viral surface antigen is HBsAg, the heterologous antigen may be from HIV, *Plasmodium falciparum, Plasmodium vivax, Plasmodium malariae* or *Plasmodium ovale*. Suitable HIV antigens for making HBsAg hybrids include envelope glycoprotein gp120 or antigenic fragments thereof [68]. Suitable *P. falciparum* antigens for making HBsAg hybrids may be based on a subunit of the circumsporozoite surface antigen ("CSP") e.g. they may include between 3 and 20 repeats of its NANP motif; and/or they may include the C-terminal region of CSP (but typically not including the final 12 amino acids from the C-terminal). For example, the invention may use the antigen known as "RTS", which contains a large portion of the C-terminal of CSP from the NF54 or 7G8 isolate of *P. falciparum* (amino acids 210 to 398, which includes 19 NANP repeats and the T cell epitope region at amino acids 367 to 390), fused to the N-terminus of HBsAg by four amino acids of the preS2 portion of HBsAg. The sequence of RTS can thus contain: (i) a N-terminus methionine residue; (ii) Met-Ala-Pro; (iii) 189 amino acids corresponding either to amino acids 210-398 of CS protein from *P. falciparum* 7G8 or to amino acids 207-395 of CS protein from *P. falciparum* NF54; (iv) Arg or Gly; (v) Pro-Val-Thr-Asn from hepatitis B Pre-S2 protein; and (vi) HBsAg.

In some embodiments of the invention, a vaccine composition does not include an influenza antigen. In some embodiments of the invention, a vaccine composition does not include an egg-derived influenza antigen. In some embodiments of the invention, a vaccine composition does not include purified influenza virus surface glycoproteins. In some embodiments of the invention, a vaccine composition is not a trivalent influenza vaccine e.g. protecting against two influenza A virus strains and one influenza B virus strain.

Pharmaceutical Compositions

Compositions made using the methods of the invention are pharmaceutically acceptable. They may include components in addition to the antigen and emulsion e.g. they will typically include one or more pharmaceutical carrier(s) and/or excipient(s). A thorough discussion of such components is available in reference 74.

The composition may include preservatives such as thiomersal or 2-phenoxyethanol. It is preferred, however, that the vaccine should be substantially free from (i.e. less than 5 µg/ml) mercurial material e.g. thiomersal-free [75,76]. Vaccines containing no mercury are more preferred. Preservative-free vaccines are particularly preferred.

To control tonicity, it is preferred to include a physiological salt, such as a sodium salt. Sodium chloride (NaCl) is preferred, which may be present at between 1 and 20 mg/ml. Other salts that may be present include potassium chloride, potassium dihydrogen phosphate, disodium phosphate dehydrate, magnesium chloride, calcium chloride, etc.

Compositions will generally have an osmolality of between 200 mOsm/kg and 400 mOsm/kg, preferably between 240-360 mOsm/kg, and will more preferably fall within the range of 290-310 mOsm/kg. Osmolality has previously been reported not to have an impact on pain caused by vaccination [77], but keeping osmolality in this range is nevertheless preferred.

Compositions may include one or more buffers. Typical buffers include: a phosphate buffer; a Tris buffer; a borate buffer; a succinate buffer; a histidine buffer; or a citrate buffer. Buffers will typically be included in the 5-20 mM range. The buffer may be in the emulsion's aqueous phase.

The pH of a composition will generally be between 5.0 and 8.1, and more typically between 6.0 and 8.0 e.g. between 6.5 and 7.5, or between 7.0 and 7.8. A process of the invention may therefore include a step of adjusting the pH of the bulk vaccine prior to packaging.

The composition is preferably sterile. The composition is preferably non-pyrogenic e.g. containing <1 EU (endotoxin unit, a standard measure) per dose, and preferably <0.1 EU per dose. The composition is preferably gluten free.

The composition may include material for a single immunization, or may include material for multiple immunizations (i.e. a 'multidose' kit). The inclusion of a preservative is preferred in multidose arrangements. As an alternative (or in addition) to including a preservative in multidose compositions, the compositions may be contained in a container having an aseptic adaptor for removal of material.

Vaccines are typically administered in a dosage volume of about 0.5 ml, although a half dose (i.e. about 0.25 ml) may be administered to children.

Compositions and kits are preferably stored at between 2° C. and 8° C. They should not be frozen. They should ideally be kept out of direct light.

Methods of Treatment, and Administration of the Vaccine

The invention provides emulsions, vaccines and kits prepared using the methods of the invention. These are suitable for use in humans, and the invention provides a method of raising an immune response in a patient, comprising the step of administering such a composition to the patient.

The invention also provides these kits and compositions for use as medicaments e.g. for raising an immune response in a patient.

The invention also provides the use of: (i) an aqueous preparation of an antigen; and (ii) an oil-in-water emulsion adjuvant as described herein, in the manufacture of a medicament for raising an immune response in a patient.

The immune response raised by these methods and uses will generally include an antibody response, preferably a protective antibody response.

Rather than being used to raise an immune response themselves, antigen-free emulsions of the invention can be used to enhance the immune response raised against a separately- or co-administered antigen.

The compositions can be administered in various ways. The most preferred immunization route is by intramuscular injection (e.g. into the arm or leg), but other available routes include subcutaneous injection, intranasal [78-80], oral [81], intradermal [82,83], transcutaneous, transdermal [84], etc.

Vaccines prepared according to the invention may be used to treat both children and adults. The patient may be less than 1 year old, 1-5 years old, 5-15 years old, 15-55 years old, or at least 55 years old. The patient may be elderly (e.g. ≥50 years old, preferably ≥65 years), the young (e.g. ≤5 years old), hospitalized patients, healthcare workers, armed service and military personnel, pregnant women, the chronically ill, immunodeficient patients, and people travelling abroad. Patients aged 0-2 years are a useful patient group (cf. reference 1). The vaccines are not suitable solely for these groups, however, and may be used more generally in a population.

Treatment can be by a single dose schedule or a multiple dose schedule. Multiple doses may be used in a primary immunization schedule and/or in a booster immunization schedule. In a multiple dose schedule the various doses may be given by the same or different routes e.g. a parenteral prime and mucosal boost, a mucosal prime and parenteral boost, etc. Administration of more than one dose (typically two doses) is particularly useful in immunologically naïve patients. Multiple doses will typically be administered at least 1 week apart (e.g. about 2 weeks, about 3 weeks, about 4 weeks, about 6 weeks, about 8 weeks, about 12 weeks, about 16 weeks, etc.).

Vaccines of the invention may be administered to patients at substantially the same time as (e.g. during the same medical consultation or visit to a healthcare professional) other vaccines.

Screening Methods

The invention provides a process for preparing an oil-in-water emulsion, comprising a step of mixing squalene with an aqueous component, wherein the squalene is assayed for the content of at least one (e.g. 1, 2, 3, 4, 5, 6, 7, 8, 9, 10, 11, 12, 13, 14 or more) PCB(s).

The invention provides a process for preparing an oil-in-water emulsion, comprising a step of mixing squalene with an aqueous component, wherein the squalene has previously been assayed for the content of at least one (e.g. 1, 2, 3, 4, 5, 6, 7, 8, 9, 10, 11, 12, 13, 14 or more) PCB(s).

The invention provides, in a process for preparing an oil-in-water emulsion comprising squalene, the improvement consisting of assaying the squalene for the content of at least one (e.g. 1, 2, 3, 4, 5, 6, 7, 8, 9, 10, 11, 12, 13, 14 or more) PCB(s).

The PCB content of the squalene is measured as discussed above. If the content meets a predetermined criterion (e.g. a maximum level of 661 picograms of PCB(s) per gram of squalene (TEQ), as discussed above) then the squalene is used to prepare the emulsion. If, on the other hand, the PCB content in the squalene does not satisfy the criterion, the squalene is rejected and the emulsion is not prepared.

Thus the invention provides a process comprising the steps of: (i) assaying a squalene sample for the content of at least one (e.g. 1, 2, 3, 4, 5, 6, 7, 8, 9, 10, 11, 12, 13, 14 or more) PCB(s); (ii) comparing the content assayed in step (i) to a predetermined maximum threshold criterion; and, if the content is lower than the threshold, (iii) using the squalene to prepare an oil-in-water emulsion.

Suitable criteria, details of PCBs, details of assays, details of preparing emulsions, etc., are all as described above.

Higher Thresholds

The invention is based on using a maximum level of 661 picograms of PCBs per gram of squalene (TEQ). Although levels comfortably below this level are routinely used, thereby offering an excellent safety profile, in some circumstances it may be possible to tolerate a higher threshold. For instance, in a public health emergency (e.g. a virulent influenza pandemic) or in certain populations (e.g. the elderly) it might be acceptable to adopt a higher threshold while maintaining an acceptable risk/benefit profile. For instance, a threshold above 661 pg/g may be acceptable in some circumstances e.g. ≤6000 pg/g, ≤5000 pg/g, ≤4000 pg/g, ≤3000 pg/g, ≤2000 pg/g, ≤1000 pg/g, ≤900 pg/g, ≤800 pg/g, or ≤700 pg/g. The threshold of 661 pg/g, however, is preferred for general use and is particularly suitable for patient populations that include children.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x is optional and means, for example, x±10%.

Where a composition contains "no" PCB, this is understood to mean that the specified PCB is not detectable by the assay being used. In practice this typically means that the PCB will either be totally absent (preferred), or else will be present at less than 1 pg PCB per gram of sample.

Unless specifically stated, a process comprising a step of mixing two or more components does not require any specific order of mixing. Thus components can be mixed in any order. Where there are three components then two components can be combined with each other, and then the combination may be combined with the third component, etc.

Where animal (and particularly bovine) materials are used in the culture of cells, they should be obtained from sources that are free from transmissible spongiform encephalopathies (TSEs), and in particular free from bovine spongiform encephalopathy (BSE). Overall, it is preferred to culture cells in the total absence of animal-derived materials.

Where a compound is administered to the body as part of a composition then that compound may alternatively be replaced by a suitable prodrug.

MODES FOR CARRYING OUT THE INVENTION

Individual lots of MF59 adjuvant (50 liters each) have been prepared by combining squalene, Span 85, Tween 80, water and citrate buffer. The components are combined in amounts that provide the desired final concentration of 5% (vol) squalene, 0.5% (vol) polysorbate 80, 0.5% (vol) Span 85 and 10 mM citrate buffer. The mixture is microfluidised at about 700 bar, and the final microfluidised mixture is filtered through a 0.2 μm filter.

To avoid the presence of harmful PCBs, squalene lots from a supplier are assessed for PCB contamination. For manufacture of MF59 a supplier has routinely been found to supply squalene with a suitably low level of PCB contamination. Contamination was tested by measuring the levels of each of fourteen PCBs (#81, #77, #123, #118, #114, #105, #126, #167, #156, #157, #169, #170, #180, #189), and these levels were then converted into TEQs using the TEFs described above.

Results of 43 such analyses are shown in Table II. The lowest TEQ was 0.103 pg PCBs per gram squalene and the highest was 188.427 pg/g. These values are well within the threshold of 661 pg/g. The sample with the highest TEQ was the only sample where PCB #169 was detected and it also had a high level (1531 pg) of PCB #126. Ignoring this sample the next highest TEQ was 92.169 pg/g. PCB #126, which has a TEF of 0.1, was detected in only 5 of the 43 samples, and if these are omitted then the highest TEQ was 21.905 pg/g. If samples containing PCB #126 are excluded from use, therefore, a TEQ 30-fold lower than the threshold of 661 pg/g can readily be achieved.

PCBs #77 and #81 were detected in only one sample each. The sample containing PCB #77 was the sample with a TEQ of 21.905 pg/g. Omitting also this sample, the maximum TEQ for the remaining 37 samples was 20.905 pg/g.

Of these 37 sample, 29 had TEQs less than 3 pg/g (i.e. >200-fold lower than the threshold). The 8 samples with TEQs between 3-21 pg/g all had TEQs above 14 pg/g, due to high levels of PCBs #170 (up to 142.2 ng/g) and #180 (up to 469.9 ng/g). The 29 lowest-TEQ samples had no more than 18.9 ng/g of PCB #170 and no more than 44.8 ng/g of PCB #180. In addition, for these 29 samples PCB #81 was not detected.

PCB #123 was seen in only 3 of the 43 samples.

19 of the 43 samples had TEQs below 1 pg/g.

In addition to measuring PCB content, levels of seven dioxins and ten furans were measured. These were seen in only 6 samples. TEQs from PCBs, dioxins and furans for these samples were as follows, measured in pg/g according to WHO 2005 TEFs:

| PCBs | Dioxins | Furans | Total |
|---|---|---|---|
| 0.539 | 0 | 0.414[#] | 0.953 |
| 0.792 | 0.273[*] | 0 | 1.065 |
| 0.987 | 0.170[*] | 0 | 1.157 |
| 1.597 | 0.461[*] | 0 | 2.058 |

| PCBs | Dioxins | Furans | Total |
|---|---|---|---|
| 2.295 | 0.253* | 0 | 2.548 |
| 0.791 | 0.435*<br>28.158+ | 0 | 29.384 |

*= OCD;
= OCDF;
+= 1,2,3,4,6,7,8-HpCDD

Thus the presence of these additional toxin contaminants in six samples did not increase the TEQ above the threshold of 661 pg/g, but the desirable absence of dioxins and furans is achievable.

All of the 43 samples had TEQs comfortably below the 661 pg/g threshold and so could be cleared for manufacture of MF59 for human use. By careful toxicological screening, though, samples with much lower TEQs can be selected, including samples free of dioxins/furans. Such screening can remove samples containing the more toxic PCBs such as #126 and #169, to give squalene with a TEQ below 25 pg/g. More stringent screening (e.g. to omit PCB #170) can select samples with TEQs of less than 3 pg/g, or even less than 1 pg/g.

It will be understood that the invention has been described by way of example only and modifications may be made whilst remaining within the scope and spirit of the invention.

REFERENCES

[1] Heilmann et al. (2006) *PLoS Med* 3(8):e311.
[2] WO90/14837.
[3] Podda & Del Giudice (2003) *Expert Rev Vaccines* 2:197-203.
[4] Podda (2001) *Vaccine* 19: 2673-2680.
[5] Storelli et al. (2005) *Mar Mollut Bull* 50:850-5.
[6] Akutsu et al. (2006) *Food Addit Contam* 23:1323-9.
[7] *Undesirable substances in seafood products—results from the monitoring activities in* 2004. Icelandic Fisheries Laboratories report 33-05.
[8] Supelco Bulletin 817C.
[9] Rubio et al. (2003) *24th Annual Meeting of SETAC*. (PH098) Immunoassay (ELISA) for the coplanar Polychlorinated Biphenyls (PCBs).
[10] *A Risk Management Strategy for PCB-Contaminated Sediments* (2001) ISBN 0-309-07321-9.
[11] WO94/26683.
[12] He et al. (2002) *J Agric Food Chem* 50:368-72.
[13] *Vaccine Design: The Subunit and Adjuvant Approach* (eds. Powell & Newman) Plenum Press 1995 (ISBN 0-306-44867-X).
[14] *Vaccine Adjuvants: Preparation Methods and Research Protocols* (Volume 42 of *Methods in Molecular Medicine* series). ISBN: 1-59259-083-7. Ed. O'Hagan.
[15] WO2008/043774.
[16] US-2007/014805.
[17] US-2007/0191314.
[18] Suli et al. (2004) *Vaccine* 22(25-26):3464-9.
[19] WO2005/097181.
[20] WO2005/089837.
[21] U.S. Pat. No. 6,692,468.
[22] WO00/07647.
[23] WO99/17820.
[24] U.S. Pat. No. 5,971,953.
[25] U.S. Pat. No. 4,060,082.
[26] EP-A-0520618.
[27] WO98/01174.
[28] Huckriede et al. (2003) *Methods Enzymol* 373:74-91.
[29] Hoffmann et al. (2002) *Vaccine* 20:3165-3170.
[30] Subbarao et al. (2003) *Virology* 305:192-200.
[31] Liu et al. (2003) *Virology* 314:580-590.
[32] Ozaki et al. (2004) *J. Virol.* 78:1851-1857.
[33] Webby et al. (2004) *Lancet* 363:1099-1103.
[34] WO97/37000.
[35] Brands et al. (1999) *Dev Biol Stand* 98:93-100.
[36] Halperin et al. (2002) *Vaccine* 20:1240-7.
[37] Tree et al. (2001) *Vaccine* 19:3444-50.
[38] Kistner et al. (1998) *Vaccine* 16:960-8.
[39] Kistner et al. (1999) *Dev Biol Stand* 98:101-110.
[40] Bruhl et al. (2000) *Vaccine* 19:1149-58.
[41] Pau et al. (2001) *Vaccine* 19:2716-21.
[42] http://www.atcc.org/
[43] http://locus.umdnj.edu/
[44] WO03/076601.
[45] WO2005/042728.
[46] WO03/043415.
[47] Hsu et al. (1999) *Clin Liver Dis* 3:901-915.
[48] WO03/002065
[49] WO01/37869
[50] WO04/005473
[51] Williamson et al. (2006) *Infection and Immunity* 74: 961-7.
[52] Loukas et al. (2005) *PLoS Med* 2(10): e295.
[53] EP-A-0139417.
[54] Harper et al. (2004) *Lancet* 364(9447):1757-65.
[55] *J Toxicol Clin Toxicol* (2001) 39:85-100.
[56] Demicheli et al. (1998) *Vaccine* 16:880-884.
[57] Stepanov et al. (1996) *J Biotechnol* 44:155-160.
[58] Covacci & Rappuoli (2000) *J. Exp. Med.* 19:587-592.
[59] WO93/18150.
[60] Covacci et al. (1993) *Proc. Natl. Acad. Sci. USA* 90: 5791-5795.
[61] Tummuru et al. (1994) *Infect. Immun.* 61:1799-1809.
[62] Marchetti et al. (1998) *Vaccine* 16:33-37.
[63] Telford et al. (1994) *J. Exp. Med.* 179:1653-1658.
[64] Evans et al. (1995) *Gene* 153:123-127.
[65] WO96/01272 & WO96/01273, especially SEQ ID NO:6.
[66] WO97/25429.
[67] WO98/04702.
[68] Berkower et al. (2004) *Virology* 321(1):75-86.
[69] von Brunn et al. (1991) *Vaccine* 9(7):477-84.
[70] Vreden et al. (1991) *Am J Trop Med Hyg* 45(5):533-8.
[71] Moelans et al. (1995) *Mol Biochem Parasitol* 72(1-2): 179-92.
[72] Stoute et al. (1997) *N Engl J Med* 336(2):86-91.
[73] Wunderlich & del Portillo (2000) *Mol Med* 6(3):238-45.
[74] Gennaro (2000) *Remington: The Science and Practice of Pharmacy.* 20th edition, ISBN: 0683306472.
[75] Banzhoff (2000) *Immunology Letters* 71:91-96.
[76] WO02/097072.
[77] Nony et al. (2001) *Vaccine* 27:3645-51.
[78] Greenbaum et al. (2004) *Vaccine* 22:2566-77.
[79] Zurbriggen et al. (2003) *Expert Rev Vaccines* 2:295-304.
[80] Piascik (2003) *J Am Pharm Assoc (Wash D.C.)*. 43:728-30.
[81] Mann et al. (2004) *Vaccine* 22:2425-9.
[82] Halperin et al. (1979) *Am J Public Health* 69:1247-50.
[83] Herbert et al. (1979) *J Infect Dis* 140:234-8.
[84] Chen et al. (2003) *Vaccine* 21:2830-6.

TABLE I

| TEFs for PCB congeners with indicated IUPAC numbers | |
|---|---|
| non-ortho substituted PCBs | |
| 77 | 0.0001 |
| 81 | 0.0003 |
| 126 | 0.1 |
| 169 | 0.03 |
| mono-ortho substituted PCBs | |
| 105 | 0.00003 |
| 114 | 0.00003 |
| 118 | 0.00003 |
| 123 | 0.00003 |
| 156 | 0.00003 |
| 157 | 0.00003 |
| 167 | 0.00003 |
| 189 | 0.00003 |

TABLE II

| TEQs from 43 squalene analyses | | | |
|---|---|---|---|
| 15.983 | 20.905 | 0.410 | 0.242 |
| 14.443 | 50.522 | 1.446 | 1.553 |
| 16.390 | 0.103 | 1.211 | 1.597 |
| 17.092 | 0.977 | 1.118 | 1.828 |
| 17.948 | 0.422 | 0.527 | 2.855 |
| 20.184 | 0.987 | 0.418 | 2.295 |
| 78.507 | 1.025 | 2.262 | 0.791 |
| 78.542 | 0.915 | 0.368 | 0.792 |
| 92.169 | 0.754 | 0.539 | 0.826 |
| 19.629 | 0.929 | 0.537 | 21.905 |
| 188.427 | 0.395 | 0.225 | |

The invention claimed is:

1. A pharmaceutical composition comprising an oil-in-water emulsion comprising squalene, wherein the emulsion comprises less than 661 picograms of polychlorinated biphenyls (PCBs) per gram of squalene (toxic equivalent; TEQ).

2. The pharmaceutical composition of claim 1, further comprising an antigen.

3. The composition of claim 1, wherein the emulsion comprises less than 10 picograms of PCBs per gram of squalene (TEQ).

4. The composition of claim 2, wherein the emulsion comprises less than 10 picograms of PCBs per gram of squalene (TEQ).

5. A pharmaceutical composition comprising an oil-in-water emulsion comprising squalene, wherein the emulsion contains no hexachlorobiphenyl.

6. The composition of claim 5, wherein the emulsion contains no 3',4,4',5,5'-hexachlorobiphenyl.

7. A pharmaceutical composition comprising an oil-in-water emulsion comprising squalene, wherein the emulsion contains no 3,3',4,4',5-pentachlorobiphenyl.

8. A pharmaceutical composition comprising an oil-in-water emulsion comprising squalene, wherein the emulsion contains no 3,3',4,4'-tetrachlorobiphenyl.

9. A pharmaceutical composition comprising an oil-in-water emulsion comprising squalene, wherein the emulsion contains no 3,4,4',5-tetrachlorobiphenyl.

10. The composition of claim 1, wherein the TEQ is calculated based on the twelve non-ortho and mono-ortho substituted PCBs.

11. The composition of claim 2, wherein the TEQ is calculated based on the twelve non-ortho and mono-ortho substituted PCBs.

12. The composition of claim 1, wherein the emulsion comprises squalene and a polyoxyethylene sorbitan ester surfactant.

13. The composition of claim 2, wherein the emulsion comprises squalene and a polyoxyethylene sorbitan ester surfactant.

14. The composition of claim 12, wherein the polyoxyethylene sorbitan ester surfactant is polysorbate 80.

15. The composition of claim 13, wherein the polyoxyethylene sorbitan ester surfactant is polysorbate 80.

16. The composition of claim 1, wherein the emulsion comprises squalene and a sorbitan ester.

17. The composition of claim 2, wherein the emulsion comprises squalene and a sorbitan ester.

18. The emulsion composition of claim 16, wherein the sorbitan ester is sorbitan trioleate.

19. The composition of claim 17, wherein the sorbitan ester is sorbitan trioleate.

20. The composition of claim 1, wherein the emulsion comprises between 5-20% by volume of oil.

21. The composition of claim 2, wherein the emulsion comprises between 5-20% by volume of oil.

22. The composition of claim 1, wherein the emulsion comprises from 0.5-5% by volume of surfactant.

23. The composition of claim 2, wherein the emulsion comprises from 0.5-5% by volume of surfactant.

24. The composition of claim 1, wherein the emulsion comprises squalene, polysorbate 80, and sorbitan trioleate.

25. The composition of claim 2, wherein the emulsion comprises squalene, polysorbate 80, and sorbitan trioleate.

26. The composition of claim 1, wherein the emulsion comprises squalene, an α-tocopherol, and polysorbate 80.

27. The composition of claim 2, wherein the emulsion comprises squalene, an α-tocopherol, and polysorbate 80.

* * * * *